United States Patent
Jelen et al.

(10) Patent No.: US 7,254,443 B2
(45) Date of Patent: Aug. 7, 2007

(54) IMPLANTABLE MEDICAL DEVICE INCLUDING A HERMETIC CONNECTOR BLOCK EXTENSION

(75) Inventors: Jeff Jelen, New Hope, MN (US); Gary W. King, Fridley, MN (US); Mark A. Christopherson, Shoreview, MN (US); Eric H. Bonde, Victoria, MN (US)

(73) Assignee: Medtronic, Inc., Minneapolis, MN (US)

( * ) Notice: Subject to any disclaimer, the term of this patent is extended or adjusted under 35 U.S.C. 154(b) by 288 days.

(21) Appl. No.: 10/861,546

(22) Filed: Jun. 4, 2004

(65) Prior Publication Data
US 2005/0033370 A1 Feb. 10, 2005

Related U.S. Application Data

(60) Provisional application No. 60/476,788, filed on Jun. 6, 2003.

(51) Int. Cl.
*A61N 1/00* (2006.01)
(52) U.S. Cl. .............. 607/36; 607/37; 607/1; 607/2; 607/6
(58) Field of Classification Search .......... 607/36, 607/37, 6, 1, 2; 439/909
See application file for complete search history.

(56) References Cited

U.S. PATENT DOCUMENTS

| | | |
|---|---|---|
| 4,595,009 A | 6/1986 | Leinders |
| 4,690,144 A | 9/1987 | Rise et al. |
| 4,791,935 A | 12/1988 | Baudino et al. |
| 5,178,161 A | 1/1993 | Kovacs |
| 5,275,171 A | 1/1994 | Barcel |
| 5,280,413 A | 1/1994 | Pai |
| 5,281,219 A | 1/1994 | Kallok |
| 5,314,495 A | 5/1994 | Kovacs |
| 5,325,870 A | 7/1994 | Kroll et al. |
| 5,336,253 A | 8/1994 | Gordon et al. |
| 5,411,532 A | 5/1995 | Mortazavi |
| 5,423,873 A | 6/1995 | Neubauer et al. |
| 5,470,345 A | 11/1995 | Hassler et al. |
| 5,470,348 A | 11/1995 | Neubauer et al. |
| 5,501,703 A | 3/1996 | Holsheimer et al. |

(Continued)

FOREIGN PATENT DOCUMENTS

EP 0 844 899 B1 7/2003

(Continued)

*Primary Examiner*—Carl Layno
*Assistant Examiner*—Natasha Patel
(74) *Attorney, Agent, or Firm*—Ingrassia Fisher & Lorenz, P.C.

(57) ABSTRACT

An implantable medical device includes a controlling device for transmitting a first series of command signals, the controlling device comprising a connector block, a first lead body including at least one electrical lead, and a hermetic encasement. The hermetic encasement includes a housing defining an interior space, an electronic network housed within the interior space and configured to receive the first set of command signals from the controlling device and output a second series of command signals based on the first set of command signals, a first set of one or more feedthrough terminals extending through the housing and directly coupling the electronic network to the connector block, and a second set of one or more feedthrough terminals extending through the housing and directly coupling the electronic network to the first lead body.

20 Claims, 6 Drawing Sheets

U.S. PATENT DOCUMENTS

| | | |
|---|---|---|
| 5,513,793 A | 5/1996 | Malmgren |
| 5,571,156 A | 11/1996 | Schmukler |
| 5,593,430 A | 1/1997 | Renger |
| 5,620,476 A | 4/1997 | Truex et al. |
| 5,643,330 A | 7/1997 | Holsheimer et al. |
| 5,679,026 A * | 10/1997 | Fain et al. .................. 439/651 |
| 5,683,435 A | 11/1997 | Truex et al. |
| 5,730,125 A * | 3/1998 | Prutchi et al. ............... 600/323 |
| 5,738,270 A | 4/1998 | Malmgren |
| 5,782,891 A | 7/1998 | Hassler et al. |
| 5,843,135 A | 12/1998 | Weijand et al. |
| 5,925,070 A | 7/1999 | King et al. |
| 5,935,155 A | 8/1999 | Humayun et al. |
| 5,999,848 A | 12/1999 | Gord et al. |
| 6,006,135 A * | 12/1999 | Kast et al. .................... 607/37 |
| 6,011,993 A | 1/2000 | Tziviskos et al. |
| 6,038,480 A | 3/2000 | Hrdlicka et al. |
| 6,052,623 A | 4/2000 | Fenner et al. |
| 6,083,252 A | 7/2000 | King et al. |
| 6,163,723 A | 12/2000 | Roberts et al. |
| 6,411,854 B1 | 6/2002 | Tziviskos et al. |
| 6,414,835 B1 | 7/2002 | Wolf et al. |
| 6,418,348 B1 | 7/2002 | Witte |
| 6,421,566 B1 | 7/2002 | Holsheimer |
| 6,473,653 B1 | 10/2002 | Schallhorn et al. |
| 2002/0128694 A1 | 9/2002 | Holsheimer |
| 2003/0077943 A1 | 4/2003 | Osypka |
| 2003/0093130 A1 | 5/2003 | Stypulkowski |
| 2003/0149456 A1 * | 8/2003 | Rottenberg et al. ........... 607/37 |

FOREIGN PATENT DOCUMENTS

| | | |
|---|---|---|
| GB | 2 124 495 A | 2/1984 |
| GB | 2 134 335 A | 8/1984 |
| GB | 2 166 608 A | 10/1985 |
| WO | WO95 19804 A1 | 7/1995 |
| WO | WO97 06853 A1 | 2/1997 |
| WO | WO97 20332 A1 | 6/1997 |
| WO | WO97 37720 A1 | 10/1997 |
| WO | WO97 38752 A2 | 10/1997 |
| WO | WO97 38752 A3 | 10/1997 |
| WO | WO99 06105 A1 | 2/1999 |
| WO | WO99 45870 A1 | 9/1999 |
| WO | WO99 49934 A1 | 10/1999 |
| WO | WO00 56677 A1 | 9/2000 |
| WO | WO03 003791 A1 | 1/2003 |
| WO | WO03 033070 A1 | 4/2003 |
| WO | WO03 041795 A1 | 5/2003 |
| WO | WO03 092807 A1 | 11/2003 |

* cited by examiner

IMPLANTABLE MEDICAL DEVICE INCLUDING A HERMETIC CONNECTOR BLOCK EXTENSION

CROSS-REFERENCES TO RELATED APPLICATIONS

This application claims the benefit of U.S. Provisional Application No. 60/476,788, filed Jun. 6, 2003.

TECHNICAL FIELD

The present invention generally relates to implantable medical devices, and more particularly relates to devices and methods that enable an implanted medical device to have diverse functions and to deliver diverse and modifiable therapies.

BACKGROUND

An implantable medical device (IMD) is an apparatus that is typically placed inside a living body to monitor certain physiological signals and provide therapy to an organ or tissue in response to the physiological signals. An example of an IMD is an implantable cardiac device (ICD) such as a pacemaker that stimulates the heart into a contraction if the sinus node is not properly pacing such contractions. Modern cardiac devices also perform many functions beyond that of pacing. For example, some ICDs perform defibrillation and cardioversion therapies. Other ICDs are able to select among several different pacing therapies depending upon the physiologic condition of a patient's heart.

A pacemaker device, as an example of an ICD, is typically implanted in a convenient location beneath a patient's skin and in the vicinity of one or more major arteries or veins. One or more electrical leads connected to the pacemaker are typically placed on or inside the patient's heart via a convenient artery or vein. The ends of the leads are placed in contact with the inside walls or the surface of one or more chambers of the heart, depending upon the particular therapies deemed appropriate for the patient.

One or more leads are adapted to carry a current from the pacemaker to the heart tissue to stimulate the heart in one of several ways, again depending upon the particular therapy being delivered. The leads are also used for sensing the physiologic signals provided by the heart to determine when to deliver a therapeutic pulse to the heart, and the nature of the pulse, e.g., a pacing pulse or a defibrillation shock. Further, one or more catheters may be connected to the IMD to deliver drugs to various body parts for pain relief, defibrillation threshold reduction, and so forth.

Distributing a variety of leads, catheters, and medical activators about a patient's body from a single IMD is a complex procedure. Further, many lead conductors and connections to the IMD are required in order for many electrodes to be distributed. Leads and connections are expensive and increase the overall IMD size. Further, as the number of leads extending from a central device increases, the overall system reliability is reduced.

Another type of IMD includes a plurality of leads for applying a pain therapy stimulus to various body areas such as the spinal column or the brain. For example, chronic pain originating in the lower back is a quite common ailment, and spinal cord stimulation is an accepted therapy for such pain. However, physicians have found that it can be difficult to properly position the spinal cord stimulation (SCS) lead to achieve good pain relief for lower back pain. Nerve fibers associated with lower back pain are only close to the dorsal column surface of the spinal cord for a short distance and are consequently difficult to locate. Physicians who consider properly treating lower back pain must develop an effective SCS technique and must learn to manipulate a stimulating lead with unusual skill and patience. Such a technique often involves implanting a stimulating device and carefully positioning at least one stimulating lead into a patient's spinal area. Even if the technique is performed properly, the leads may need to be repositioned over time. Repositioning the stimulating leads is typically an invasive surgical procedure that carries risks and requires great patience, care, and skill.

Accordingly, it is desirable to provide a simple and cost efficient system for distributing leads and associated medical activators from an IMD to one or more body locus. In addition, it is desirable to reduce the number of components associated with an IMD and thereby improve the reliability of the IMD and the associated system. It is further desirable to provide a system for non-invasively relocating an electrical field after the system is implanted. Furthermore, other desirable features and characteristics of the present invention will become apparent from the subsequent detailed description and the appended claims, taken in conjunction with the accompanying drawings and the foregoing technical field and background.

BRIEF SUMMARY

An implantable hermetic connector block extension is provided for coupling a lead body with a connector block that is part of an implantable medical device that transmits a first series of command signals. The hermetic connector block extension includes a housing defining an interior space, an electronic network housed within the interior space and configured to receive the first set of command signals from the controlling device and output a second series of command signals based on the first set of command signals, a first set of one or more feedthrough terminals extending through the housing and adapted to directly couple the electronic network to the connector block, and a second set of one or more feedthrough terminals extending through the housing and adapted to directly couple the electronic network to the first lead body.

An implantable medical assembly is also provided. The assembly comprises a first lead body comprising at least one electrical lead, and a hermetic connector block extension coupled to the first lead body and adapted to be coupled to the connector block. The hermetic connector block extension comprises a housing defining an interior space, an electronic network housed within the interior space and configured to receive the first set of command signals from the implantable medical device and output a second series of command signals based on the first set of command signals, a first set of one or more feedthrough terminals extending through the housing and adapted to directly couple the electronic network to the connector block, and a second set of one or more feedthrough terminals extending through the housing and directly coupling the electronic network to the first lead body.

An implantable medical device is also provided. The device comprises a controlling device for transmitting a first series of command signals, the controlling device comprising a connector block, a first lead body comprising at least one electrical lead, and a hermetic encasement. The hermetic encasement comprises a housing defining an interior space, an electronic network housed within the interior space and configured to receive the first set of command signals from the controlling device and output a second series of command signals based on the first set of command signals, a first set of one or more feedthrough terminals extending through the housing and directly coupling the electronic network to the connector block, and a second set of one or more feedthrough terminals extending through the housing and directly coupling the electronic network to the first lead body.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The present invention utilizes integrated electronics in a connector block extension that is located between an IMD and a lead body. For convenience, unless otherwise indicated the term "IMD" is inclusive of any implantable medical device capable of administering any of a number of therapies to a patient's heart or other organs and tissues. The connector block extension is tailored for specific functions and can be interchanged with other connector block extensions tailored for other specific functions. The interchangeable connector block extensions allow the IMD to be manufactured inexpensively as a generically functioning shell module that can cooperate with different connector block extensions that are easily plugged into the IMD 10.

The figures illustrate embodiments of the present invention in the context of a cardiac pacemaker, it being understood that the invention certainly has applicability to many other types of IMDs. For example, the present invention may be used in conjunction with any suitable medical lead having a sensor, stimulator or other treatment device adapted for a sensing and/or treatment application. For convenience, all types of such sensors, stimulators and treatment devices will be referred to herein as "medical activator units." Examples of suitable medical activator units include drug delivery devices, stimulating electrodes, and mechanical sensors such as thermocouples, strain gauges, sonomicrometers and accelerometers, and biosensors such as calcium sensors or other chemical sensors.

Figure 1:
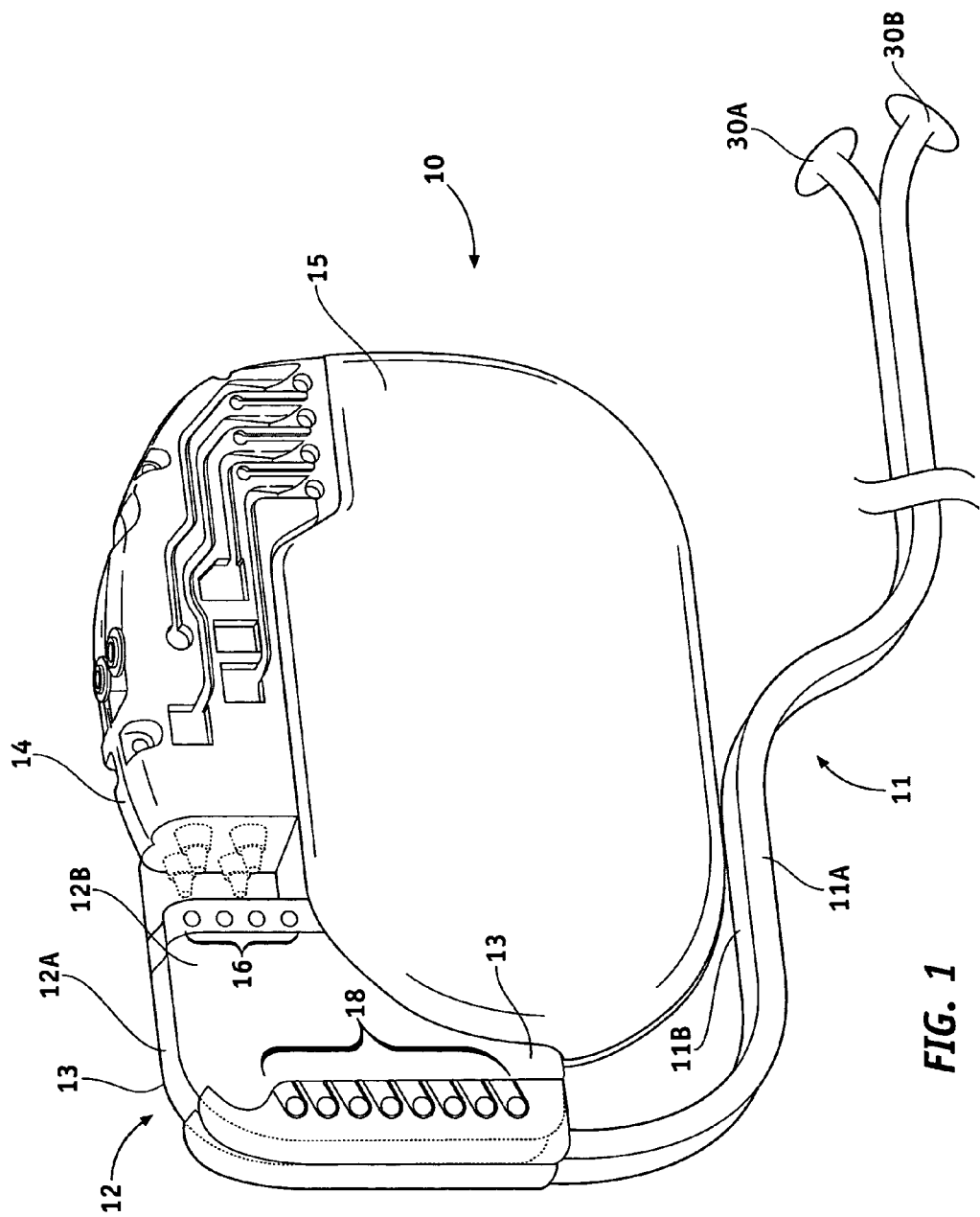
FIG. 1 is a perspective view of an assembly including an IMD, a lead body, and a connector block extension according to an embodiment of the present invention.

As depicted in FIG. 1, one or more leads 11a, 11b collectively identified as lead body 11 are electrically coupled to an IMD 10 that is adapted to be implanted at a medically suitable location in a patient's body during use. Each lead body 11 is electrically coupled to the IMD 10 using "smart extensions" 12a, 12b that are collectively identified as a connector block extension 12. The connector block extension 12 is a hermetic encasement that is directly coupled with an IMD connector block 14 having electrical contacts for coupling with extension 12. The connector block extension 12 is also directly coupled with the lead body 11 at a second connection port 18. The connector block extension 12 houses an electronic network that may include a memory for storing programs that, when executed, enable the electronic network to communicate with and control multiple medical activator units 30a, 30b, although only one such medical activator unit is shown for each lead body 11a, 11b in FIG. 1. The connector block extension 12 may further include at least one energy source such as a battery to power the electronic network and/or the medical activator units 30. The connector block extension 12 might also derive its energy by storing electrical pulses from the IMD 10. The connector block extension 12 and its components will be described in greater detail below.

Figure 2:
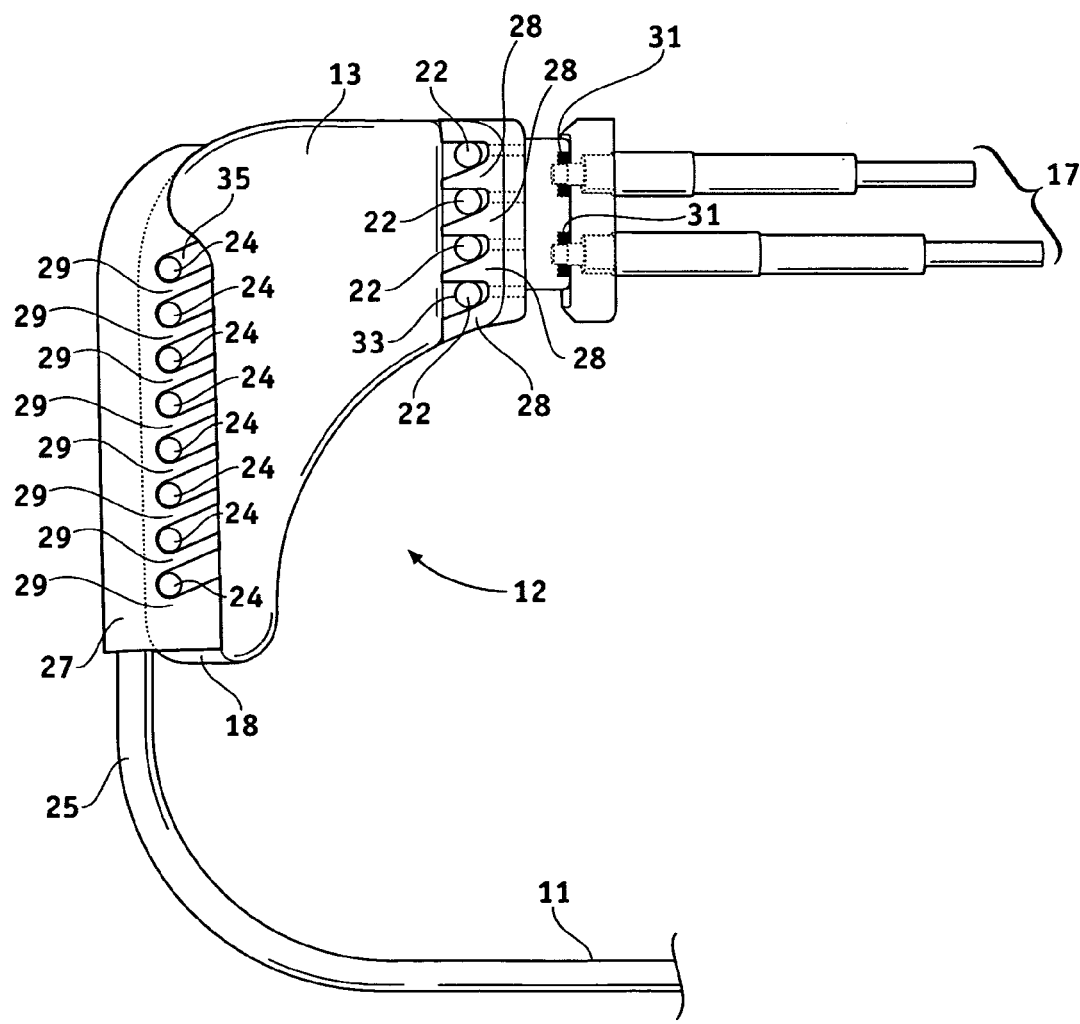
FIG. 2 is a side view of a connector block extension according to an embodiment of the present invention along with electrical connectors coupled thereto.
Figure 3:
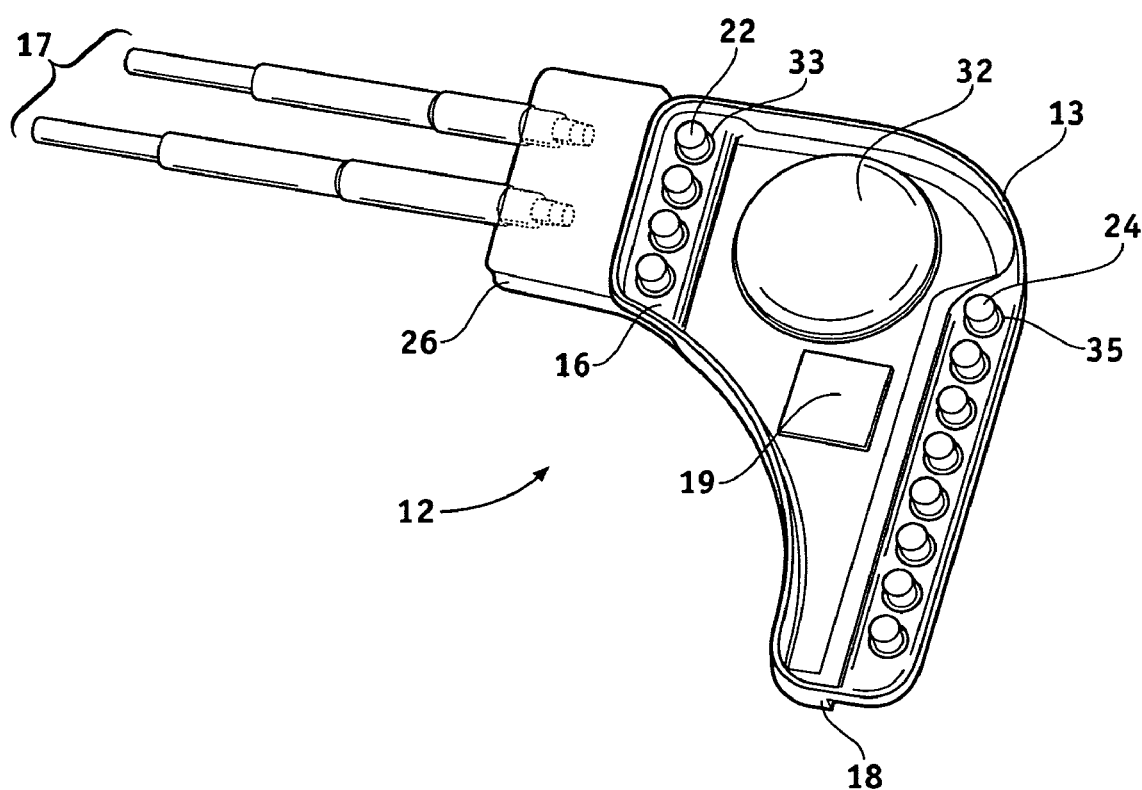
FIG. 3 is a perspective view of a connector block extension interior according to an embodiment of the present invention.

FIGS. 2 and 3 respectively depict detailed exterior and interior views of the connector block extension 12. The connector block extension 12 includes two or more molded parts 13 that are joined together to define an interior space in which the electronic network circuitry, stand-alone sensory and/or therapy devices, and a power source may be enclosed. The molded parts 13 can be formed of any suitable biocompatible material. In an exemplary embodiment of the invention, the molded parts 13 are composed of a ceramic material that includes one or more of titanium, niobium, and niobium 46-titanium. In another exemplary embodiment the molded parts 13 are composed of a biocompatible polymer such as biocompatible polyurethane. The ceramic material is preferably formed in layers, including integral layers of dielectric material for EMI shielding. The molded parts 13 can be joined using any conventional joining method, preferably using a laser, furnace, or a thermo-compression micro-joining process. In an exemplary embodiment of the invention, the molded parts 13 are connected using a micro-joining material such as gold, indium, active gold braze alloys, platinum alloys, titanium-copper-nickel active brazes, or at least one biocompatible sealing glass composition.

The connector block extension 12 is coupled to the IMD 10 using a first connector 26 that is adapted to engage with the connection port 16. The first connector 26 includes a first set of contacts 28 and a second set of contacts 31. The first set of contacts 28 is formed from a conductive and biocompatible metal such as gold or platinum, with each contact being positioned to match up with one of the connector block extension contacts 22. The connector block extension contacts 22 are exteriorly disposed on the connection port 16 and are also formed from a conductive and biocompatible metal. The second set of contacts 31 is also formed from a conductive and biocompatible metal.

The connector block extension 12 is coupled to the lead body 11 using a second connector 27 that is adapted to engage with the connection port 18. The second connector 27 includes an insulative material 25 that surrounds and protects at least a proximal portion of the lead body 11. A set of contacts 29 is provided on the second connector 27 and is formed from a conductive and biocompatible metal. Each of the contacts in the set 29 is positioned to match up with connector block extension contacts 24 that are exteriorly disposed on the connection port 18 and are also formed from a conductive and biocompatible metal.

The connectors 26, 27 illustrated In FIG. 2 represent only one of many possible devices for directly coupling the connector block extension 12 with an IMD 10 and a lead body 11. Other attachment devices may be used, including setscrews or a custom-shaped cup that physically holds the parts together.

The connector block contacts 22, 24 are feedthrough conductors that extend through openings 33, 35 in the connector block extension molded parts 13. A braze material may be applied at the contact/molding interfaces in order to provide a hermetic seal around the contacts 22, 24. Portions of the contacts 22, 24 are disposed outside the connector block extension 12 and are consequently exposed to the encasement exterior, thereby allowing the lead body 11 to be coupled to the connector block extension contacts 22, 24.

As mentioned above, the connector block extension 12 is a hermetic encasement for at least one energy source 32, and integrated electrical circuitry/components 19 that may include electronic intelligence and stand-alone therapeutic devices that operate in an independent and self-contained manner. The connector block extension 12 is disposed between the lead body 11 and the IMD 10, and consequently enables stand-alone devices and also components that are controlled by the IMD 10 to be separate from, but also in direct communication with the IMD 10.

Although the energy source 32 may be a simple battery, the connector block extension 12 may be powered by dedicated conductive lines from the IMD 10. In another embodiment, the energy source 32 harvests or rectifies power from the IMD stimulation pulses and stores the same in order to power the connector block extension 12 and/or the medical activator units 30. In yet another embodiment, the connector block extension 12 is temporarily powered by way of an external magnetic field or RF energy.

Figure 4:
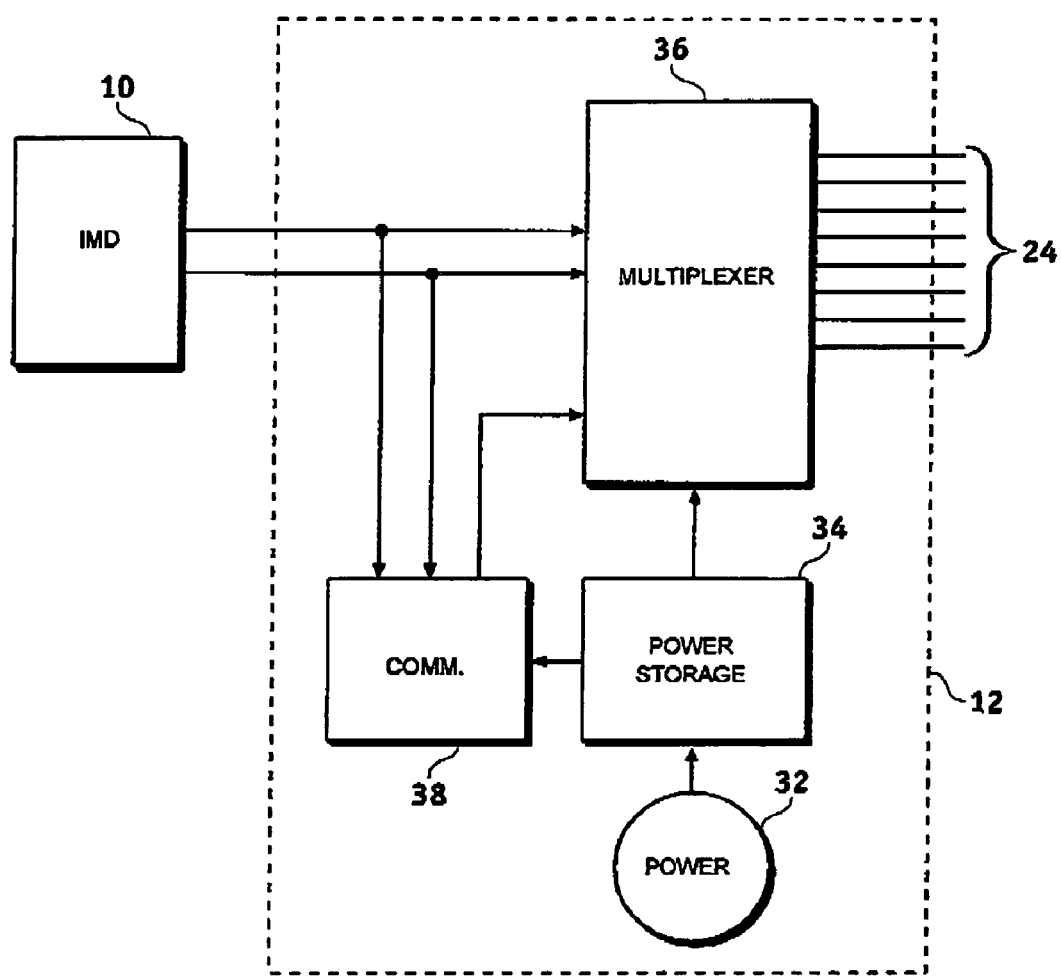
FIG. 4 is a diagram illustrating a circuitry design for an electrode multiplexer and components associated therewith according to an embodiment of the present invention.

One exemplary application of an IMD that includes a connector block extension 12 is a neurological stimulator lead system. In such a system, package-integrated high density inputs/outputs are mounted inside the connector block extension 12 and an electrode multiplexer selectively carries out coordinated signals to an array of electrodes that apply currents to nerves or other body tissues. FIG. 4 is a diagram illustrating a circuitry design for an electrode multiplexer and components associated therewith. The specific design illustrated in FIG. 4 is for converting signals from two outputs from IMD 10 to signals controlling eight electrodes, although the invention is not limited by the number of electrodes on the leads or channels a multiplexer is configured to accommodate with regard to inputting or outputting.

A multiplexer 36 inside the connector block extension 12 receives signals from electrical outputs on the IMD 10. Communication circuitry 38 decodes commands included in the two IMD stimulation signal pulses and transmits the decoded pulses to the multiplexer 36. The multiplexer includes a plurality of switches that route electrical pulses to one or more of the eight connector block extension outputs 24 according to commands in the decoded IMD signals transmitted from the communication circuitry 38. One method by which the communication circuitry 38 receives and transmits switch settings involves the physician or other user evoking a series of low amplitude stimulation pulses that include multiplexer switch setting commands. Another method incorporates a receiver that temporarily powers up in response to a stimulation burst evoked by the physician or other user, and powers down after multiplexer switch setting commands are received and carried out. An exemplary method involves programmed communication circuitry 38 that automatically invokes brief 0.2 volt stimulation pulses anytime that a physician or other authorized user transmits a switch setting command to a receiver. A confirmation signal is then sent to the user interface, and the physician or other user must confirm the switch setting change. The confirmation signal preferably indicates the lead impedance and the electrode configuration to be initiated. Upon confirmation of the switch setting change, the communication circuitry 38 then communicates the desired switch settings to the multiplexer 36. Multiplexer 36 or communication circuitry 38 shall have means for storing the parameters of the therapeutic pulses between times that control signals are sent, and also should the entire device be turned off for periods of time.

A power source 32 is electrically coupled to a power storage device 34, and the power storage device 34 provides operating power to the multiplexer 36, the communication circuitry 38, and other circuitry or devices that are included in the connector block extension 12. In one exemplary embodiment of the invention, the power source 32 and the power storage device 34 are combined as a battery. In another exemplary embodiment the power storage device 34 is a capacitor that is charged and can store a sufficient amount of power to the multiplexer 36 and other circuitry or devices. A capacitor that has minimal current drain can maintain a sufficient charge for weeks without need for a recharge. The capacitor is selected according to factors such as the minimum stimulation voltage, and the voltage needed to control the multiplexer 36 and other circuitry or devices. The power storage device 34 receives power from the power source 32 which can be a battery or a power source included in the IMD 10 or derived from IMD pulses.

Because the connector block extension 12 is disposed between the IMD 10 and the lead body 11, a larger number of electrodes can originate from the connector block extension 12 than would originate from the IMD 10 itself according to the IMD construction. Further, the connector block extension 12 contains circuitry that would conventionally be disposed in the IMD 10. These advantages allow the IMD 10 to be much smaller due to a limited amount of circuitry and output ports required by the IMD 10. In addition, the IMD 10 can be easily manufactured as a generically functioning shell module that can cooperate with different connector block extensions that are easily plugged into the IMD 10 and are configured to perform specific functions or to expand the functionality of the IMD 10.

Figure 5:
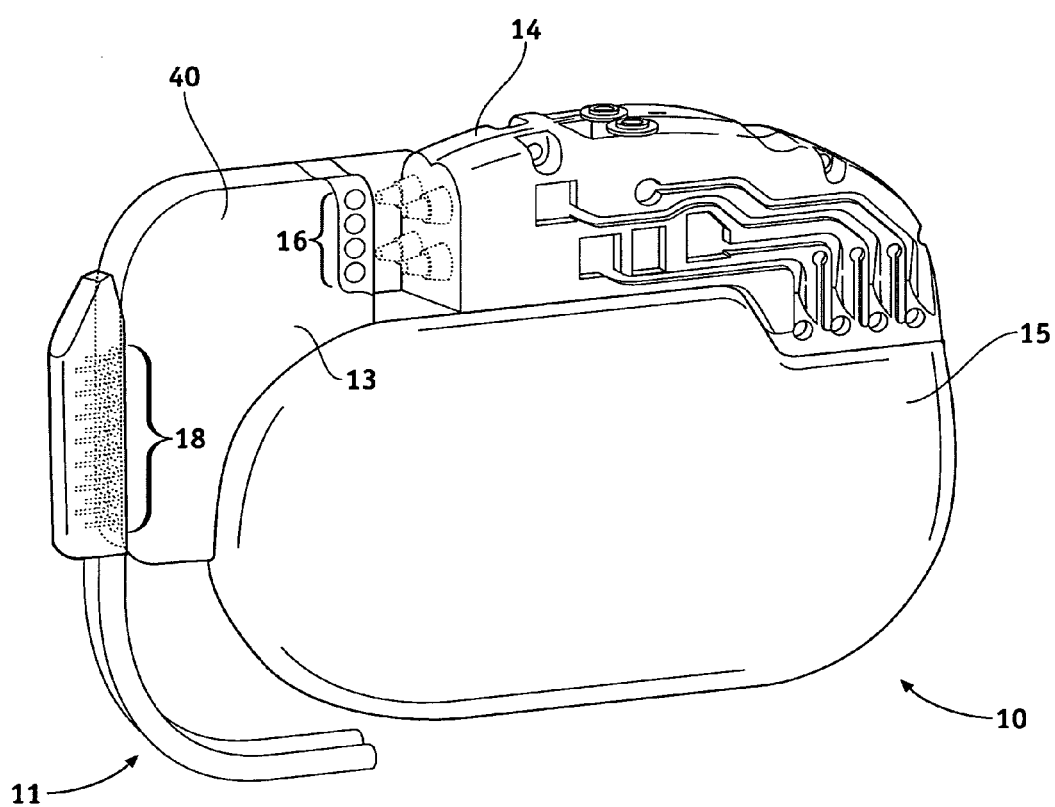
FIG. 5 is a perspective view of an IMD and a dual connector block extension according to an embodiment of the present invention.
Figure 6:
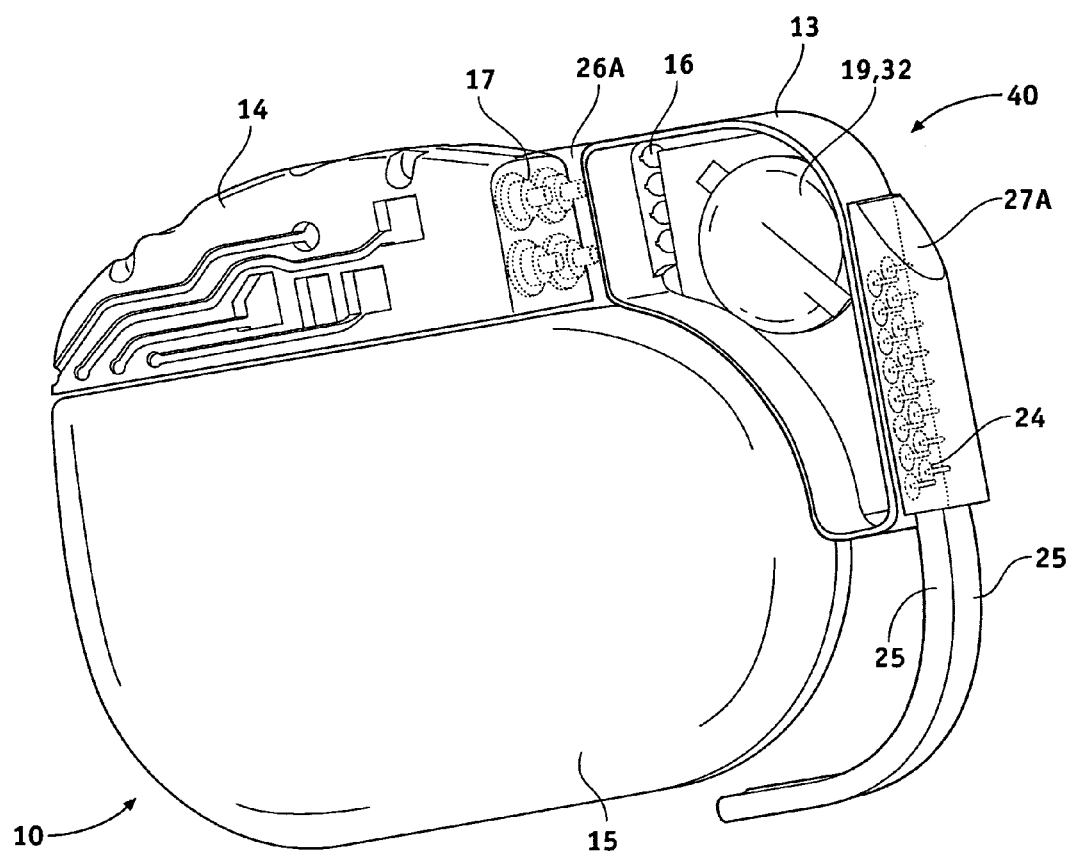
FIG. 6 is a perspective view of an IMD and a dual connector block extension interior according to an embodiment of the present invention.

FIGS. 5 and 6 illustrate another embodiment of an IMD assembly that includes an IMD 10 electrically coupled to a dual connector block extension 40. The specific assembly illustrated in FIGS. 6 and 7 is for converting signals from four outputs to signals controlling sixteen electrodes, although this embodiment is not limited by the number of electrodes or channels that the dual extension 40 is configured to accommodate with regard to inputting or outputting. The dual extension 40 and the IMD 10 coupled thereto include many of the same elements in the earlier-described embodiments, and identical components are identified with identical reference numerals.

The dual extension 40 includes a first connector 26a that is adapted to engage with the connection port 16. The first connector 26a includes contacts (not shown), similar or identical to the contacts 28 in FIG. 2, that are positioned to match up with the connector block extension contacts 22. The first connector 26a also includes contacts (not shown), similar or identical to contacts 31 in FIG. 2, that are positioned to receive or otherwise engage with the four IMD contacts 17.

The dual extension 40 is coupled to the lead body 11 using a second connector 27a that includes an insulating material 25 that surrounds and protects at least a proximal portion of a lead body. A set of contacts (not shown), similar or identical to the set of contacts 29 in FIG. 2, is provided on the second connector 27a and is positioned to match up with sixteen connector block extension contacts 24 that are exteriorly disposed on the dual extension 40.

The connector block contacts 22, 24 are feedthrough conductors that extend through openings 33, 35 in the connector block extension molded parts 13. A braze material may be applied at the contact/molding interfaces in order to provide a hermetic seal around the contacts 22, 24. Portions of the contacts 22, 24 are disposed outside the connector block extension 12 and are consequently exposed to the encasement exterior, thereby allowing lead body 11 and the IMD contacts 17 to be coupled to the contacts 22, 24.

Communication components including receivers, transmitters, and associated circuitry are enclosed within the connector block extension 12 as part of the circuitry 19 to enable external interaction with the electronic intelligence in the connector block extension 12. A physician or other authorized user may optimize current vectors to targeted body tissue, stimulation pulse width, stimulation pulse rate, stimulation pulse amplitude, and other factors by programming the electronic intelligence in advance to select different electrode configurations. During a treatment, the user may further optimize current vectors to targeted body tissue, stimulation pulse width, stimulation pulse rate, stimulation pulse amplitude, and other factors by transmitting command signals to the communication circuitry. Alternatively, the IMD 10 may automatically control the circuitry 19 within the connector block extension 12. The communication circuitry may receive programming or other commands directly from a user-controlled external device, or indirectly via the IMD 10. In an exemplary embodiment of the invention the programming or other commands are transmitted to the communication circuitry by wireless means, although it is clearly within the scope of the invention for communication signals to also be transmitted using a dedicated communication line, or modulated on top of a dedicated power line. For instance, pulse patterns that are provided as part of therapy stimulation may be used to program or control the circuitry 19, or communication signals of very small amplitude may be modulated on top of such power or therapy signals.

A similar exemplary application includes a cardiac padding lead with multiple ring electrodes that that are individually controlled and operated and allow for varied ring-tip separation. Another similar exemplary application of the present invention includes a multiple physiologic sensor array (EcOG) for treating epilepsy, for example. In this or other embodiments, a drug pump may be among the electrical components 19 mounted inside the connector block extension 12. At least one catheter extending through the connector block extension 12 and in fluid communication with the pump would deliver drugs to targeted areas.

The foregoing description details how the present invention utilizes integrated electronics in a connector block extension located between an IMD and a lead body. The connector block extension is tailored for specific functions and can be replaceable with other connector block extensions tailored for other functions, allowing the IMD to be manufactured inexpensively as a generically functioning shell module that can cooperate with different connector block extensions that are easily plugged into the IMD and coupled to a lead body. A multiplexer in the connector block extension makes placement of downstream electrodes on body tissue less critical because more electrodes can be selected or deselected for maximum therapeutic efficacy. Communication circuitry in the connector block extension allows a physician or other authorized user to manipulate the electrode array without requiring an invasive surgical procedure. Other stand alone devices and circuitry can be disposed in the connector block extension and manipulated by a user so that therapy can be modified as needed in an efficient manner.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An implantable medical device, comprising:
   a controlling device for transmitting a first set of command signals, the controlling device comprising a connector block;
   a first lead body comprising at least one electrical lead; and
   a hermetic encasement, separable from the controlling device and the connector block, the hermetic encasement comprising:
      a housing defining an interior space,
      an electronic network housed within the interior space and configured to receive the first set of command signals from the controlling device and output a second set of command signals that are different than and based on the first set of command signals,
      a first set of one or more feedthrough terminals extending through the housing and directly coupling the electronic network to the connector block, and
      a second set of one or more feedthrough terminals extending through the housing and directly coupling the electronic network to the first lead body.

2. The device according to claim 1, further comprising at least one medical activator coupled to one of the electrical leads, the medical activator unit being selected from the group consisting of a stimulating electrode, a thermocouple, a strain gauge, a sonomicrometer, an accelerometer, a biosensor, and a drug-delivery device.

3. The device according to claim 1, wherein the number of feedthrough terminals in the first set is less than the number of feedthrough terminals in the second set.

4. The device according to claim 3, wherein the electronic network comprises:
   a multiplexer including a set of switches adapted to transmit electrical pulses to each of the leads in the lead body, and communication circuitry that decodes the first set of command signals into switch setting commands and transmits the switch setting commands to the multiplexer.

5. The device according to claim 1, wherein the hermetic encasement further comprises a drug delivery device responsive to the electronic network, and a catheter extending through the housing and in fluid communication with the fluid pump.

6. The device according to claim 1, wherein the hermetic encasement further comprises an energy source for providing power at least to the electronic network.

7. The device according to claim 1, wherein said hermetic encasement further comprises a transmitter and a receiver for transmitting and receiving user command signals originating from a source external to the implantable medical device, the transmitter and receiver being in electrical communication with the electronic network.

8. An implantable medical assembly adapted to be coupled to a connector block that is part of an implantable medical device that transmits a first set of command signals, the assembly comprising:
- a first lead body comprising at least one electrical lead; and
- a hermetic connector block extension separable from the connector bock and the implantable medical device, the connector block extension being coupled to the first lead body and adapted to be coupled to the connector block, comprising:
  - a housing defining an interior space,
  - an electronic network housed within the interior space and configured to receive the first set of command signals from the implantable medical device and output a second set of command signals that are different than and based on the first set of command signals,
  - a first set of one or more feedthrough terminals extending through the housing and adapted to directly couple the electronic network to the connector block, and
  - a second set of one or more feedthrough terminals extending through the housing and directly coupling the electronic network to the first lead body.

9. The assembly according to claim 8, further comprising at least one medical activator coupled to one of the electrical leads, the medical activator unit being selected from the group consisting of a stimulating electrode, a thermocouple, a strain gauge, a sonomicrometer, an accelerometer, a biosensor, and a drug-delivery device.

10. The assembly according to claim 8, wherein the number of feedthrough terminals in the first set is less than the number of feedthrough terminals in the second set.

11. The assembly according to claim 10, wherein the electronic network comprises:
- a multiplexer including a set of switches adapted to transmit electrical pulses to each of the leads in the lead body, and
- communication circuitry that decodes the first set of command signals into switch setting commands and transmits the switch setting commands to the multiplexer.

12. The assembly according to claim 8, wherein the hermetic connector block extension further comprises a drug delivery device responsive to the electronic network, and a catheter extending through the housing and in fluid communication with the fluid pump.

13. The assembly according to claim 8, wherein the hermetic connector block extension further comprises an energy source for providing power at least to the electronic network.

14. The assembly according to claim 8, wherein the hermetic encasement further comprises a transmitter and a receiver for transmitting and receiving user command signals originating from a source external to the implantable medical device, the transmitter and receiver being in electrical communication with the electronic network.

15. An implantable hermetic connector block extension adapted to be directly coupled to a lead body and directly coupled to a connector block that is part of an implantable medical device that transmits a first set of command signals, the hermetic connector block extension comprising:
- a housing, separable from the connector block and the implantable medical device, the housing defining an interior space;
- an electronic network housed within the interior space and configured to receive the first set of command signals from the controlling device and output a second set of command signals that are different than and based on the first set of command signals;
- a first set of one or more feedthrough terminals extending through the housing and adapted to directly couple the electronic network to the connector block; and
- a second set of one or more feedthrough terminals extending through the housing and adapted to directly couple the electronic network to the first lead body.

16. The hermetic connector block extension according to claim 15, wherein the number of feedthrough terminals in the first set is less than the number of feedthrough terminals in the second set.

17. The hermetic connector block extension according to claim 16, wherein the electronic network comprises:
- a multiplexer including a set of switches adapted to transmit electrical pulses to each of the leads in the lead body, and
- communication circuitry that decodes the first set of command signals into switch setting commands and transmits the switch setting commands to the multiplexer.

18. The hermetic connector block extension according to claim 15, further comprising a drug delivery device responsive to the electronic network, and a catheter extending through the housing and in fluid communication with the fluid pump.

19. The hermetic connector block extension according to claim 15, wherein the hermetic connector block extension further comprises an energy source for providing power at least to the electronic network.

20. The hermetic connector block extension according to claim 15, further comprising a transmitter and a receiver for transmitting and receiving user command signals originating from a source external to the implantable medical device, the transmitter and receiver being in electrical communication with the electronic network.

* * * * *